(12) United States Patent
Li et al.

(10) Patent No.: US 7,651,839 B2
(45) Date of Patent: Jan. 26, 2010

(54) METHOD OF OPTIMIZING AMPLIFICATION IN PCR

(75) Inventors: Haikuo Li, Shanghai (CN); Jiehuan Huang, Shanghai (CN); Junhong Lv, Shanghai (CN); Xiaodong Zhang, Shanghai (CN); Jun Hu, Shanghai (CN); Zhizhou Zhang, Tianjin (CN); Chunhai Fan, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 11/322,764

(22) Filed: Dec. 29, 2005

(65) Prior Publication Data

US 2006/0166240 A1    Jul. 27, 2006

(30) Foreign Application Priority Data

Dec. 29, 2004   (CN) .................. 2004 1 0099186
Feb. 3, 2005    (CN) .................. 2005 1 0023780

(51) Int. Cl.
*C12Q 1/68*    (2006.01)
*C12P 19/34*   (2006.01)

(52) U.S. Cl. ........................... 435/6; 435/91.2
(58) Field of Classification Search ............ None
See application file for complete search history.

(56) References Cited

U.S. PATENT DOCUMENTS 7,300,755 B1 *  11/2007  Petersdorf et al. .............. 435/6
2002/0090649 A1 *  7/2002  Chan et al. .................... 435/7.1
2003/0087242 A1 *  5/2003  Mirkin et al. .................. 435/6

OTHER PUBLICATIONS

Li et al. Enhancing the efficiency of a PCR using gold nanoparticles. Nucleic Acids Res. (2005) 33:e184, pp. 1-10.*

* cited by examiner

*Primary Examiner*—Gary Benzion
*Assistant Examiner*—David C Thomas
(74) *Attorney, Agent, or Firm*—Raymond Y. Chan; David and Raymond Patent Firm

(57) ABSTRACT

The present invention discloses a method for optimizing PCR amplification by adding elementary substance material into PCR system, wherein the elementary substance material is selected from a group consisting of element titanium, element nickel, element bismuth, element stibium, element selenium, element chromium, and a mixture of the group. This new method is more effective than conventional amplifying method and could be widely employed in many fronts, especially in multiplex PCR, two-round PCR, low-copy PCR, long-term PCR and rapid PCR.

18 Claims, 7 Drawing Sheets

METHOD OF OPTIMIZING AMPLIFICATION IN PCR

BACKGROUND OF THE PRESENT INVENTION

1. Field of Invention

The present invention relates to a method for optimizing amplification in polymerase chain reaction (PCR), and more particularly, relates to a method for adding element gold, titanium, nickel, bismuth, stibium, selenium, and chromium into polymerase chain reactions to enhance the specificity of the reaction, to increase the yield of target molecules, and to shorten the reaction time.

2. Description of Related Arts

PCR is a quick and easy method for generating a large amount of copies of any DNA target in vitro. Due to the fact that the PCR mechanism is rather complicated, certain interference side effects would be unavoidable in actual practices. For example, there could be mispairing between primers and templates, which cause non-specific amplifications (which is shown as a broad molecular size distribution and non-specific trailing streak) thus resulting to lower amplification specificity and efficiency. Even worse, such side effects could cause the failure of the amplification reaction. The improvement of the PCR amplification specificity is not only determined by the optimizing design of the primer sequence, but also is depended on the optimization of the reaction system and procedure. It is proven that by adding additives, such as formamide, glycerin, DMSO (dimethyl sulfoxide) into the reaction system, the non-specific amplification problems could be ameliorated to certain extent. Unfortunately, the treating effects of above mentioned additives are not ideal in many fields. Moreover, some added components, such as DMSO would inhibit the activities of the polymerase.

U.S. Pat. No. 5,646,019 'method for producing primer nucleic acid template' introduced a method for adding heat-stable single-stranded nucleic acid binding protein (SSB) into the PCR system, wherein SSB protein is only combined with single-stranded DNA, instead of double-stranded DNA. Such method is adapted to inhibit the non-specific amplification. Therefore, the optimization of the PCR amplification could be achieved. However, the techniques adapted for extracting purified SSB are rather complicated. What is more, the reagent purity is required to be higher thus worsening the cost issue. As a result, the reagent kit available in the market would be rather costly. Commonly, the reagent kit prepared with such method will be 6-7 times more expensive than common PCR reagent products. On the other hand, to maintain the biological activities of single-stranded nucleic acid binding protein, the PCR reagent should be reserved at −20° C. temperatures. Finally, the active period of such PCR reagent is rather short.

SUMMARY OF THE PRESENT INVENTION

A primary object of the present invention is to provide an improved PCR amplification method for enhancing the specificity of the reaction, for increasing the yield of the target molecules, and for shortening the reaction time.

Another object of the present invention is to provide an improved PCR amplification method, which is universally applicable to a variety of PCR systems.

Another object of the present invention is to provide an improved PCR amplification method, which is effective to optimize PCR system with simple and inexpensive manner, wherein the optimized materials can be reserved easily and applied widely.

Another object of the present invention is to provide an improved PCR amplification method, wherein the optimized materials can be conveniently removed from the PCR system.

Accordingly, to achieve above mentioned objects, the present invention provides PCR amplification method, comprising the following step:

adding elementary substance materials into PCR system as optimized materials, wherein the elementary substance materials are selected from a group consisting of element gold, element titanium, element nickel, element bismuth, element stibium, element selenium, element chromium and a mixture of the group.

These and other objectives, features, and advantages of the present invention will become apparent from the following detailed description, the accompanying drawings, and the appended claims.

DETAILED DESCRIPTION OF THE PREFERRED EMBODIMENT

Figure 1:
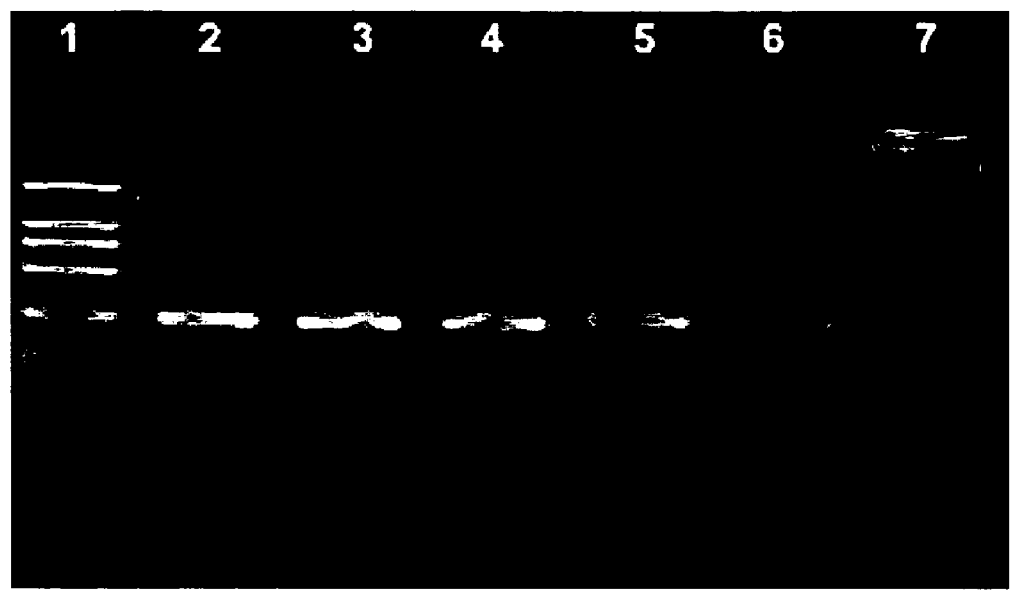
FIG. 1 illustrates the products of common PCR by using gold sheet as optimized material run on an agarose gel according to the preferred embodiment of the present invention.

The present invention introduces a method for enhancing specificity and efficiency of PCR amplification, the method comprises the following step (a) for adding elementary substance materials into PCR system as optimized materials, wherein the elementary substance materials are selected from a group consisting of element gold, element titanium, element nickel, element bismuth, element stibium, element selenium, element chromium, and a mixture of the group.

Accordingly, the step (a) further comprises the following sub-steps.

(a-1) preparing elementary substance materials which are used as optimized materials;

First of all, the elementary substance materials mentioned above could be embodied as different shapes and forms, such as filaments, sheets, particles, powder, colloid or any other irregular shape and form. According to the preferred embodiment, the forms of elementary substance materials mentioned above could be prepared in lab or obtained from the market, wherein no particular requirements or limitation is set for the size of powder and colloid materials. It is noted that colloid materials could be prepared according to conventional method.

Secondly, the optimized materials mentioned above regardless of the shapes and forms are washed by sterilized water and then by absolute ethyl alcohol. It is noted that colloid materials need not washing.

(a-2) sterilizing the optimized materials;

That is to say, the elementary substances materials mentioned above are adapted to be sterilized through ultra-violet radiation, dry-method or wet-method. It is noted that colloid materials need not sterilizing.

(a-3) Optimizing PCR system;

According to the preferred embodiment of the present invention, the PCR system optimization refers to adding a predetermined amount of any kind of elementary substance materials mentioned above into PCR system to perform PCR amplification. The predetermined quantity refers to the quantity of optimized materials added into the 25 μL PCR system. In case the PCR system is greater or less than 25 μL, the quantity of added materials should be proportionally adjusted.

Furthermore, the optimized materials in filament and sheet form are prepared with certain length and shape thus enabling such shaped materials adapted to a PCR tube containing 25 μL solution, wherein the optimized materials are fully immersed within the solution and the height of the solution surface is not higher than 0.6 cm from the bottom of the PCR tube. If the solution surface is higher than 0.6 cm, an evenly distributed temperature will be difficult to achieve. For element gold, a minimum optimal surface area should be at least 4 mm$^2$; for other elementary substance materials, a minimum optimal surface area should be at least 2 mm$^2$ to get an effective optimizing effect.

Accordingly, the spherical particles should be added into the PCR system depending on its size, i.e. one or more particles could be added into the PCR tube containing 25 μL solution, wherein the optimized materials are fully immersed within the solution and the height of the solution surface is not higher than 0.6 cm from the bottom of the PCR tube. It is noted that the amount of the optimized materials added into the PCR system should be based on the total surface area which is at least 2 mm$^2$ to get an effective optimizing effect.

Finally, it is shown in 25 μL reaction system, the suitable amount of 200-300 mesh titanium powder is ranged from 20 μg to 1000 μg and the optimal amount of such titanium powder is ranged from 50 μg to 800 μg. For chromium powder, the suitable amount of 200 mesh size is ranged from 450 μg to 1500 μg and the optimal amount of such chromium powder is ranged from 600 μg to 1200 μg. Generally, the added amount for powder materials should be ranged from 50 μg to 500 μg. For gold powder, the adding amount is no less than 2 mg.

To obtain a precise amount, the elementary substance materials in powder form should be weighted, and then added into the sterilized water to get fully dispersion, thereafter, certain amount of suspended solution can be added into the PCR system.

In ultimate 25 μL PCR system, the suitable amount of colloid gold is ranged from 0.06 μL to 6.0 μL, wherein the suitable amount of 5 nm colloid gold with 0.01% HAuCl$_4$ concentration is 0.06 μL-0.5 μL, the optimal amount is 0.08 μL-0.16 μL. The suitable amount of 10 nm colloid gold with 0.01% HAuCl$_4$ concentration is 0.5 μL-2.5 μL, the optimal amount is 0.5 μL-1.6 μL. The suitable amount of 20 nm colloid gold with 0.01% HAuCl$_4$ concentration is 0.8 μL-6.0 μL, the optimal amount is 0.8 μL-3.5 μL. For other optimized materials in colloid form, the suitable amount is 0.5 μL-4 μL. It is worth to mention that the PCR amplification could be performed according to conventional method.

In ultimate 25 μL PCR system, any kind of elementary substance materials mentioned above can be selected to compound a mixture, which is used as optimized materials. The suitable amount of every component in the mixtures is varied, due to its form. For the mixtures in powder form, the suitable amount is ranged from 50 μg to 5000 μg; for the mixture in colloid form, the suitable amount is 0.06 μL-6 μL; and for the mixture of powder and colloid, wherein the suitable amount of powder is from 20 μg to 5000 μg and the suitable amount of colloid is 0.02 μL-6 μL.

(a-4) analyzing the PCR products.

The agarose electrophoresis procedure is used to check the PCR products, and the optimizing effects can be shown by comparing the optimized sample with the control sample.

(a-5) removing the optimized materials from the PCR system;

For those optimized materials in filament, sheet, and other irregular form, the solution could be directly aspirated so as to separate the optimized materials; for powder and particle formed optimized materials, the PCR system is centrifuged at a low speed and the supernatant can be harvested; for colloids formed materials, the PCR system is frozen overnight at a temperature of −20° C. first, and then is centrifuged with a high speed to obtain the supernatant.

The agarose gel electrophoresis could be embodied as the conventional methods.

Conclusively, PCR in this invention refers to varied kinds of PCR, including common PCR, multiplex PCR, two-round PCR, low-copy PCR, rapid PCR and so on.

Optimized materials mentioned in this invention also adapt to optimize other reactions which are based on PCR mechanism or polymerase.

In short, the amplification method introduced by the present invention is more effective than conventional amplifying method. Furthermore, the amplifying method of the present invention could be widely employed in many fronts, and the optimized materials are simple to be removed from the PCR system. And more importantly, the optimized materials used in the present invention, such as element titanium, element bismuth, element nickel, element stibium, element selenium, element chromium and their mixture would not cause any inhibition for the polymerase, and could be reserved at a temperature of 4° C. without losing its activity.

From another perspective, the amplifying method of the present invention is comparatively cheaper with respect to the conventional amplifying method. For example, commercial titanium powder costs only one hundredth of the single stranded DNA binding protein. There is no particular equipment requirement for embodying the amplifying method.

EXAMPLES

In all examples of this patent, the PCR reaction volume is 25 μL.

In all examples of this patent, the PCR system is made up as the table below:

| Components | Volume |
| --- | --- |
| Takara Ex Taq polymerase (5 U/μL) | 0.25 μL |
| 10 × PCR buffer solution | 2.5 μL |
| dNTPs (10 mM) | 0.75 μL |
| $Mg^{2+}$ (250 mM) | 0.35 μL |
| Primer 1 (1 μM) | 2.5 μL |
| Primer 2 (1 μM) | 2.5 μL |
| Template | 1 μL |
| Optimized Material | varied |
| Double Distilled $H_2O$ | added up to 25 μL |

In the examples of this patent, the optimized materials mentioned above regardless of the shapes and forms are washed by sterilized water and then by absolute ethyl alcohol. Thereafter, these optimized materials are sterilized through ultra-violet radiation. It is noted that colloid materials need not washing and sterilizing.

Example 1

Optimizing Common PCR by Using Gold Sheet as Optimized Material

In this example, 50 ng λ DNA is used as the template in PCR, and two primers are used to amplify a 283-bp segment. The sequences of these two primers are: P1: 5'-GGCTTCG-GTCCCTTCTGT-3', P2: 5'-CACCACCTGT-TCAAACTCTGC-3'.

The amplifications are performed as follows: 94° C. for 2 minutes (pre-heating), followed by 30 cycles of 94° C. for 30 seconds (denaturing), 58° C. for 1 minutes (annealing) and extend at 72° C. for 45 seconds; followed by a final extension at 72° C. for 5 minutes, and thereafter the products of PCR reactions are analyzed by agarose gel electrophoresis.

As shown in FIG. 1, each reaction of lane 2, 3, and 4 contains a piece of gold sheet, whose size is 2 mm×2 mm; reactions of lane 5, 6 and 7 do not contain gold sheet; and lane 1 is DNA marker (2000 bp, 1000 bp, 750 bp, 500 bp, 250 bp, and 100 bp). The amplification results of PCR containing gold sheet (lane 2, 3, and 4) show the single predominant band corresponding to the 283-bp target. However, the amplification results of PCR without gold sheet (lane 5, 6 and 7) show non-specific PCR products as a broad molecular size distribution. Notably, an increase in specificity by using gold sheet is seen in this experiment.

Example 2

Optimizing low copy PCR by using gilded silicon as optimized material

In this example, the template used in PCR is pBR322 plasmid DNA, and two primers are used to amplify a 342-bp segment. The sequences of these two primers are:

```
P1: 5'-CTAACGGATTCACCACTCCAAGAA-3';

P2: 5'-GACTTCCGCGTTTCCAGACTTTAC-3'.
```

The amplifications are performed as follows: 94° C. for 2 minutes (pre-heating), followed by 45 cycles of 94° C. for 30 seconds (denaturing), 58° C. for 1 minutes (annealing) and extend at 72° C. for 45 seconds; followed by a final extension at 72° C. for 7 minutes, and thereafter the products of PCR reactions are analyzed by agarose gel electrophoresis.

Figure 2:
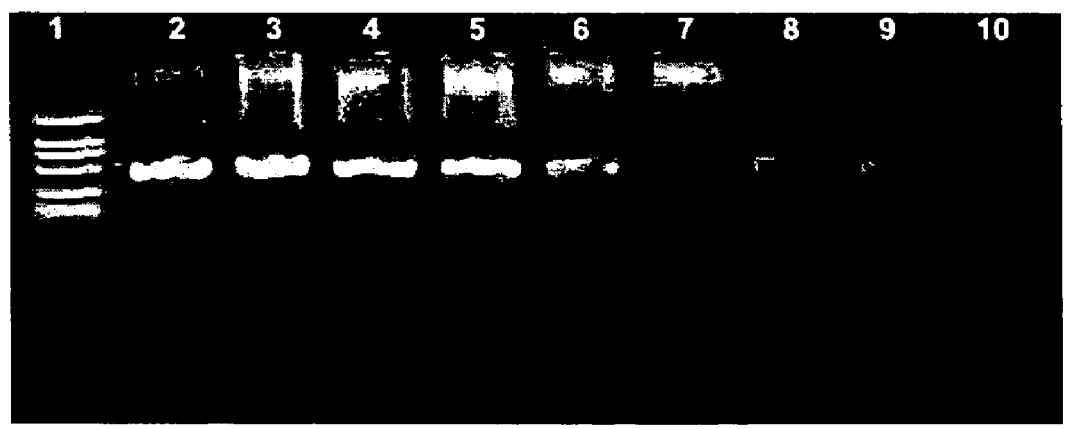
FIG. 2 illustrates the products of low copy PCR by using gilded silicon as optimized material run on an agarose gel according to the preferred embodiment of the present invention.

As shown in FIG. 2, lane 2 is the result of the PCR containing $10^5$ copies of pBR322 plasmids as template; lane 3 is the result of the PCR containing $10^4$ copies of pBR322 plasmids as template; lane 4 is the result of the PCR containing $10^3$ copies of pBR322 plasmids as template; lane 5 is the result of the PCR containing $10^2$ copies of pBR322 plasmids as template; lane 6 is the result of the PCR containing 10 copies of pBR322 plasmids as template; lane 7, 8, 9 are the results of the PCR containing nearly one pBR322 plasmid as template; lane 10 is the result of the PCR without template, and lane 1 is DNA marker (2000 bp, 1000 bp, 750 bp, 500 bp, 250 bp, and 100 bp). All templates used in this example are prepared by dilution. None of the PCR system from lane 2 to 7 contains optimized material, while every PCR system from lane 8 to 10 contains a piece of gilded silicon as optimized material. The gilded silicon used in this example is 4 mm in length and 1.5 mm in width, and only one side is gilded. With the reference of FIG. 2, the results of PCR without gilded silicon (lane 2-7) show severe tailing, while the results of single molecule PCR containing gilded silicon as optimized material (lane 8, 9) show single clear band. Notably, an increase in specificity by using gilded silicon is seen in this example.

Example 3

Optimizing Single Molecule PCR by Using Colloid Gold as Optimized Material

In this example, the template used in this example is single DNA fragment prepared from pBR322 plasmid by nanomanipulation: imaging, dissecting and picking up single DNA fragment with the help of atomic force microscopy (AFM). The primers are the same as those of example 2.

The amplifications are performed as follows: preheating at 95° C. for 2 minutes; 10 cycles of 95° C. for 30 seconds (denaturing), 65° C. for 3 minutes (annealing) and 72° C. for 45 seconds (extension); 10 cycles of 95° C. for 30 seconds (denaturing), 65° C. touch-down to 58° C. for 1 minute (annealing) and 72° C. for 45 seconds (extension); 30 cycles of 94° C. for 30 seconds (denaturing), 58° C. for 1 minute (annealing) and 72° C. for 45 seconds (extension); finally, additional extension at 72° C. for 7 minutes, and thereafter the products of PCR reactions are analyzed by agarose gel electrophoresis.

Colloid gold (10 nm, 0.01% HAuCl$_4$) is purchased from Sigma.

Figure 3:
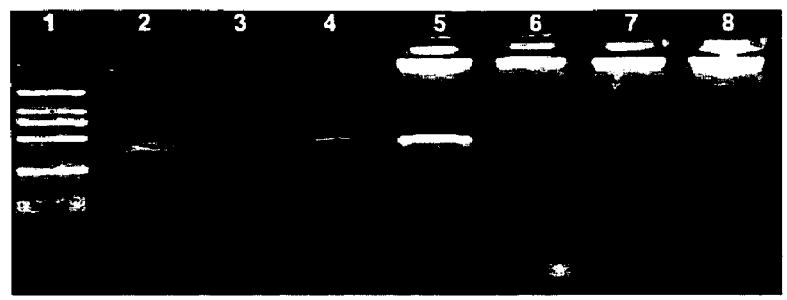
FIG. 3 illustrates the products of single molecule PCR by using colloid gold in as optimized material run on an agarose gel according to the preferred embodiment of the present invention.

As shown in FIG. 3, each reaction of lane 2, 3, and 4 contains single molecule DNA template prepared by nanomanipulation and 1 μL colloid gold as optimized material; reaction of lane 5 contains 10 copies of pBR322 plasmid prepared by dilution as template but no colloid gold; reaction of lane 6 contains single molecule DNA prepared by nanomanipulation but no colloid gold; reactions of lane 7 and 8 contain neither template DNA or colloid gold; and lane 1 is DNA marker (2000 bp, 1000 bp, 750 bp, 500 bp, 250 bp, and 100 bp). The amplification result of PCR containing colloid gold shows a single predominant band corresponding to the 384-bp target (lane 2, 3, and 4). However, the amplification results of PCR without colloid gold (lane 6) show non-specific PCR products as a broad molecular size distribution. Notably, an increase in specificity by using colloid gold is seen in this experiment.

Example 4

Optimizing multiplex PCR by using colloid gold as optimized material

In this example, 50 ng λ DNA is used as the template in PCR, and 8 pairs of primers are used to amplify 8 segments: 159 bp, 283 bp, 485 bp, 573 bp, 660 bp, 785 bp, 942 bp and 1240 bp. The sequences of these primers are:

```
Pair 1:
P1: 5'-GGATGACCCCTCCAGCG-3';
P2: 5'-CCGTAAACTCCACCCTTCG-3'

Pair 2:
P1: 5'-GATGCTTGAACCCGCCTAT-3';
P2: 5'-GCCTGTCGTGGTCCGTC-3'

Pair 3:
P1: 5'-GGCTTCGGTCCCTTCTGT-3';
P2: 5'-CACCACCTGTTCAAACTCTGC-3'

Pair 4:
P1: 5'-TGGAGCGTGAGGAATGGG-3';
P2: 5'-GCCGTGTTCGGGTAGCA-3'

Pair 5:
P1: 5'-CTCGCTCATAACAGACATTCACT-3';
P2: 5'-TCAACATCTTCTCGGGCATA-3'

Pair 6:
P1: 5'-GCACAAGTCCGACAACCC-3';
P2: 5'-GCTGAGGAGATAAATAATAAACGAG-3'

Pair 7:
P1: 5'-CAAAACTAAGGGCATAGACAATAA-3';
P2: 5'-TGGTTCAGAAGATAAATCGCTC-3'

Pair 8:
P1: 5'-CGGAACATCTCGGTAACTGC-3';
P2: 5'-CGTCGCTGTCTCGCCAC-3'
```

The amplifications are performed as the same as Example 1, and thereafter the products of PCR reactions are analyzed by agarose gel electrophoresis.

Colloid gold (10 nm, 0.01% HAuCl$_4$) is purchased from Sigma.

Figure 4:
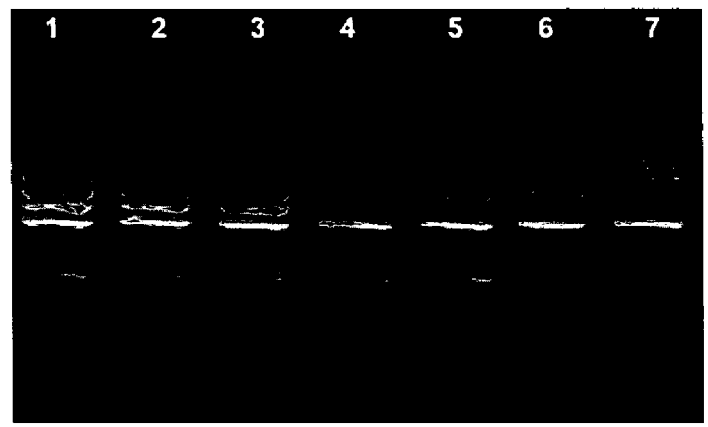
FIG. 4 illustrates the products of multiplex PCR by using colloid gold as optimized material run on an agarose gel according to the preferred embodiment of the present invention.

As shown in FIG. 4, reactions of lane 1, 2, and 3 do not contain colloid gold; each reaction of lane 4, 5, and 6 contains 1 μL colloid gold as optimized material; and lane 7 is DNA marker (1500 bp, 1000 bp, 900 bp, 800 bp, 700 bp, 600 bp, 500 bp, 400 bp, 300 bp, 200 bp, and 100 bp). The amplification result of PCR containing colloid gold shows clear bands corresponding to the targets (lane 4, 5, and 6). However, the amplification results of PCR without colloid gold (lane 1, 2, and 3) show non-specific PCR products as tailing bands. Notably, an increase in specificity by using colloid gold is seen in this experiment.

Example 5

Optimizing long-term PCR by using colloid gold as optimized material

In this example, 50 ng λ DNA is used as the template in PCR, and two primers are used to amplify a 4200-bp segment.

```
P1: 5'-ACGCTCGTCGTTTGGTATGGC-3';
P2: 5'-CCGGCTGGCTGGTTTATTGC-3'
```

The amplifications are performed as follows: 95° C. for 2 minutes (pre-heating), followed by 40 cycles of 94° C. for 30 seconds (denaturing), 58° C. for 1 minutes (annealing) and extend at 72° C. for 3 minutes; followed by a final extension at 72° C. for 10 minutes, and thereafter the products of PCR reactions are analyzed by agarose gel electrophoresis.

Colloid gold (10 nm, 0.01% HAuCl$_4$) is purchased from Sigma.

Figure 5:
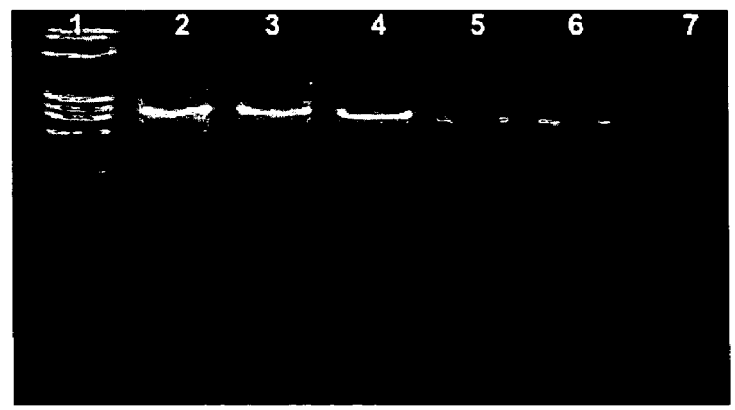
FIG. 5 illustrates the products of long-term PCR by using colloid gold as optimized material run on an agarose gel according to the preferred embodiment of the present invention.

As shown in FIG. 5, reactions of lane 2, 3 and 4 do not contain colloid gold; each reaction of lane 5 and 6 contains 1 μL colloid gold as optimized material; lane 1 is DNA marker (15000 bp, 10000 bp, 7500 bp, 5000 bp, 2500 bp, 1000 bp, and 250 bp); and lane 7 is the result of the PCR without template. The amplification result of PCR containing colloid gold shows a single predominant band corresponding to the 4200-bp target (lane 5 and 6). However, the amplification results of PCR without colloid gold (lane 1, 2, and 3) show non-specific PCR products as a broad molecular size distribution. Notably, an increase in specificity by using colloid gold is seen in this experiment.

Example 6

Optimizing two-round PCR by using colloid gold in different sizes as optimized material Herein, an error-prone two-round PCR is used as model system. In the first round, a 283-bp sequence is amplified using 50 ng λ DNA template with 30 PCR cycles; in the second round PCR, this 283-bp DNA is employed as the template for the other 30-cycle PCR amplification sequence, and the final concentration of the template in the second PCR system is 20 ngmL$^{-1}$. The primers are the same as those of example 1.

The amplification program is performed as the same as example 1, and thereafter the products of PCR reactions are analyzed by agarose gel electrophoresis.

Colloid gold (5 nm, 10 nm, and 20 nm; 0.01% HAuCl$_4$) is purchased from Sigma.

Figure 6:
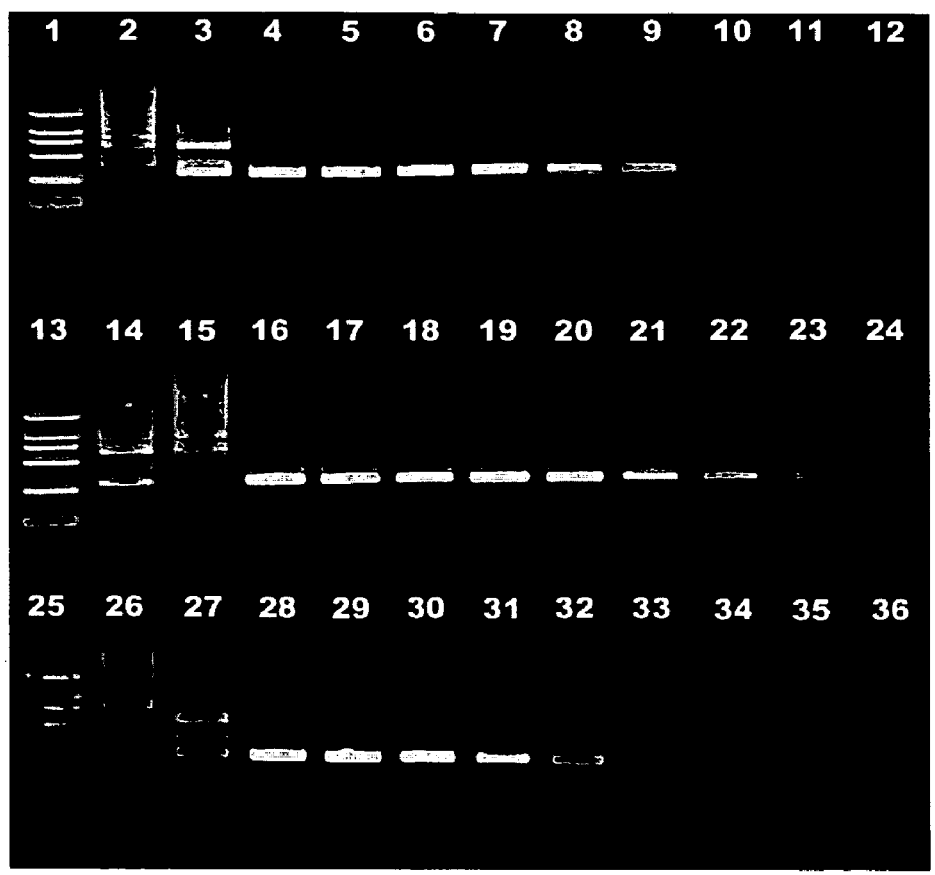
FIG. 6 illustrates the products of two-round PCR by using colloid gold of different sizes as optimized material run on an agarose gel according to the preferred embodiment of the present invention.

As shown in FIG. 6, the amounts of 5 nm colloid gold contained in reactions are as below: 0.03 μL (lane 3), 0.06 μL (lane 4), 0.08 μL (lane 5), 0.1 μL (lane 6), 0.12 μL (lane 7), 0.14 μL (lane 8), 0.16 μL (lane 9), 0.25 μL (lane 10), and 0.5 μL (lane 11). The amounts of 10 nm colloid gold contained in reactions are as below: 0.2 μL (lane 15), 0.5 μL (lane 16), 0.6 μL (lane 17), 0.8 μL (lane 18), 1.0 μL (lane 19), 1.3 μL (lane 20), 1.6 μL (lane 21), 2.0 μL (lane 22), and 2.5 μL (lane 23). The amounts of 20 nm colloid gold contained in reactions are as below: 0.5 μL (lane 27), 0.8 μL (lane 28), 1.5 μL (lane 29), 2.0 μL (lane 30), 2.5 μL (lane 31), 3.0 μL (lane 32), 3.5 μL (lane 33), 4.0 μL (lane 34), and 6.0 μL (lane 35). The reactions of lane 2, 14 and 26 do not contain colloid gold; lane 12, 24, and 36 are the results of the PCR without templates; and lane 1, 13 and 25 are DNA marker (2000 bp, 1000 bp, 750 bp, 500 bp, 250 bp, and 100 bp). The amplification result of PCR containing colloid gold shows a single predominant band corresponding to the 283-bp target. However, the amplification results of PCR without colloid gold show non-specific PCR products as a broad molecular size distribution. Notably, an increase in specificity by using colloid gold is seen in this experiment.

The amounts of different size colloid gold needed to optimize the reaction are different. The suitable amount of 5 nm colloid gold is from 0.06 µL to 0.5 µL, and the preferred amount of 5 nm colloid gold is from 0.08 µL to 0.16 µL. The suitable amount of 10 nm colloid gold is from 0.5 µL to 2.5 µL, and the preferred amount of 10 nm colloid gold is from 0.5 µL to 1.6 µL. The suitable amount of 20 nm colloid gold is from 0.8 µL to 6.0 µL, and the preferred amount of 20 nm colloid gold is from 0.8 µL to 3.5 µL.

Example 7

Optimizing two-round PCR by using colloid gold as optimized material and quantifying the target product of PCR.

In this example, the same two-round PCR system as Example 6 is used.

Every round of amplification program is performed as the same as Example 1, and thereafter the products of PCR reactions are analyzed by agarose gel electrophoresis.

Colloid gold (10 nm, 0.01% $HAuCl_4$) is purchased from Sigma.

Figure 7:
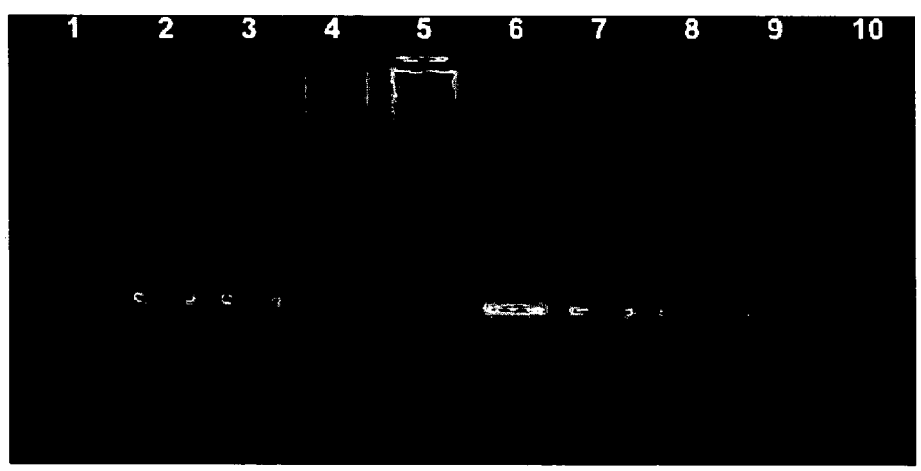
FIG. 7 illustrates the products of two-round PCR by using colloid gold as optimized material run on an agarose gel according to the preferred embodiment of the present invention.

As shown in FIG. 7, reactions of lane 2, 3, 4 and 5 do not contain colloid gold; each reaction of lane 6, 7, 8 and 9 contains 1 µL colloid gold as optimized material; lane 10 is the result of the PCR without template; and lane 1 is DNA marker (2000 bp, 1000 bp, 750 bp, 500 bp, 250 bp, and 100 bp). The amplification result of PCR containing colloid gold shows a single predominant band corresponding to the 283-bp target (lane 6, 7, 8 and 9). However, the amplification results of PCR without colloid gold show non-specific PCR products as a broad molecular size distribution (lane 2, 3, 4 and 5). The FIG. 7 is analyzed by photodensitometry, and the product yields of land 6, 7, 8 and 9 are bigger by 0.8, 0.5, 0.2 and 0.2 folds respectively than the yields of lane 2. Notably, an increase in specificity and yield by using colloid gold is seen in this experiment.

Example 8

Optimizing common PCR by using titanium powder as optimized material

In this example, the components of PCR system are the same as those of example 1.

The amplifications are performed as the same as Example 1, and thereafter the products of PCR reactions are analyzed by agarose gel electrophoresis.

The size of titanium powder used in this example is 200-300 mesh.

Figure 8:
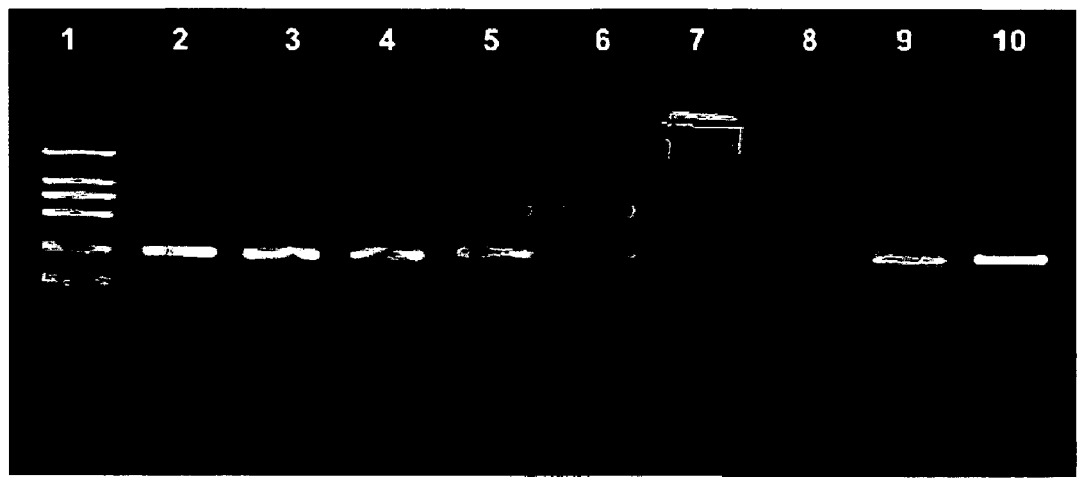
FIG. 8 illustrates the products of common PCR by using titanium powder as optimized material run on an agarose gel according to the preferred embodiment of the present invention.

As shown in FIG. 8, each reaction of lane 2, 3 and 4 contains 1 µL colloid gold; each reaction of lane 5, 6 and 7 does not contain optimized material; each reaction of lane 8, 9 and 10 contains 800 µg, 400 µg and 100 µg titanium powder respectively; and lane 1 is DNA marker (2000 bp, 1000 bp, 750 bp, 500 bp, 250 bp, and 100 bp). The amplification result of PCR containing colloid gold (lane 2, 3 and 4) and titanium powder (lane 9 and 10) shows a single predominant band corresponding to the 283-bp target. However, the amplification results of PCR without titanium powder show non-specific PCR products as a broad molecular size distribution. With the reference of the results of lane 8, 9 and 10, 100 µg and 400 µg titanium powder optimizes PCR well while 800 µg titanium powder shows a little inhibition for PCR in this example.

Example 9

Optimizing two-round PCR by using titanium powder as optimized material

In this example, the same two-round PCR system as Example 6 is used.

Every round of amplification program is performed as the same as Example 1, and thereafter the products of PCR reactions are analyzed by agarose gel electrophoresis.

The size of titanium powder used in this example is 200-300 mesh.

Figure 9:
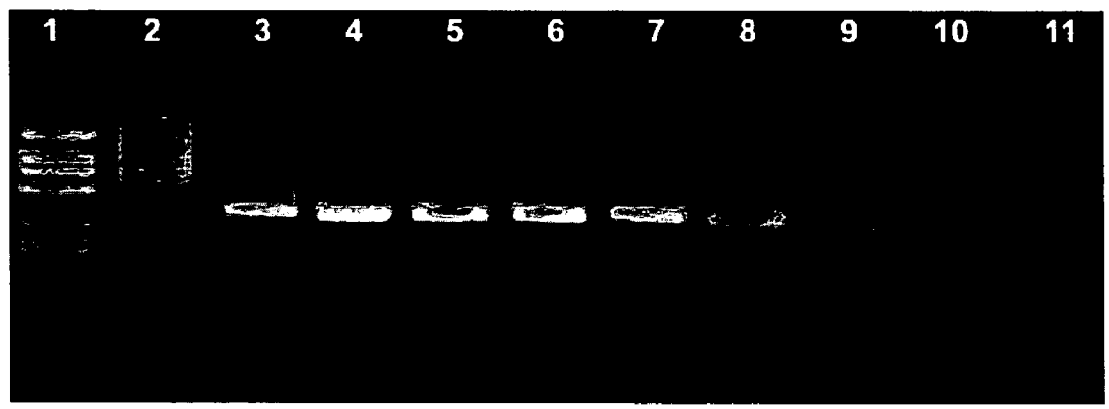
FIG. 9 illustrates the products of two-round PCR by using titanium powder as optimized material run on an agarose gel according to the preferred embodiment of the present invention.

As shown in FIG. 9, the amounts of 200-300 mesh titanium powder contained in reactions are as below: 20 µg (lane 3), 50 µg (lane 4), 100 µg (lane 5), 200 µg (lane 6), 300 µg (lane 7), 400 µg (lane 8), 800 µg (lane 9) and 1000 µg (lane 10), and the reaction of lane 2 does not contain optimized material, the reaction of lane 11 does not contain DNA template, and lane 1 is DNA marker (2000 bp, 1000 bp, 750 bp, 500 bp, 250 bp, and 100 bp). The amplification result of PCR containing suitable amount of titanium powder shows a single predominant band corresponding to the 283-bp target. However, the amplification results of PCR without titanium powder show non-specific PCR products as a broad molecular size distribution. The suitable amount of titanium powder is from 20 µg to 1000 µg, and the preferred amount of titanium powder is from 50 µg to 800 µg.

Example 10

Optimizing multiplex PCR by using titanium filaments as optimized material

In this example, the same multiplex PCR system as Example 4 is used.

The amplification program is performed as the same as Example 1, and thereafter the products of PCR reactions are analyzed by agarose gel electrophoresis.

The titanium filaments used in this example is 3 mm in length, and 0.5 mm in diameter.

Figure 10:
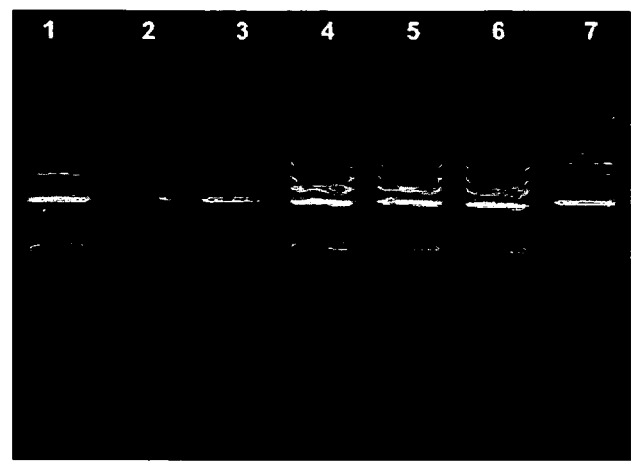
FIG. 10 illustrates the products of two-round PCR by using titanium filament as optimized material run on an agarose gel according to the preferred embodiment of the present invention.

As shown in FIG. 10, each reaction of lane 1, 2, and 3 contains a piece of titanium filament as optimized material; reactions of lane 4, 5, and 6 do not contain titanium filament; and lane 7 is DNA marker (1500 bp, 1000 bp, 900 bp, 800 bp, 700 bp, 600 bp, 500 bp, 400 bp, 300 bp, 200 bp, and 100 bp). The amplification result of PCR containing titanium filament shows clear bands corresponding to the targets. However, the amplification results of PCR without titanium filament show non-specific PCR products as tailing bands. Notably, an increase in specificity by using titanium filament is seen in this experiment.

Example 11

Optimizing two-round PCR by using element nickel, element bismuth, element stibium, element selenium and element chromium as optimized materials In this example, the same two-round PCR system as Example 6 is used.

Every round of amplification program is performed as the same as Example 1, and thereafter the products of PCR reactions are analyzed by agarose gel electrophoresis.

The nickel filament used in this example is 3.2 mm in length, and is 0.8 mm in diameter; the bismuth spherical particle used in this example is 0.1-0.2 mm in diameter, and about 12 mg in weight; the stibium spherical particle used in this example is 0.1-0.2 mm in diameter, and about 30 mg in weight; the amount of selenium powder used in this example is 400 μg; and the amount of chrome powder used in this example is 800 μg.

Figure 11:
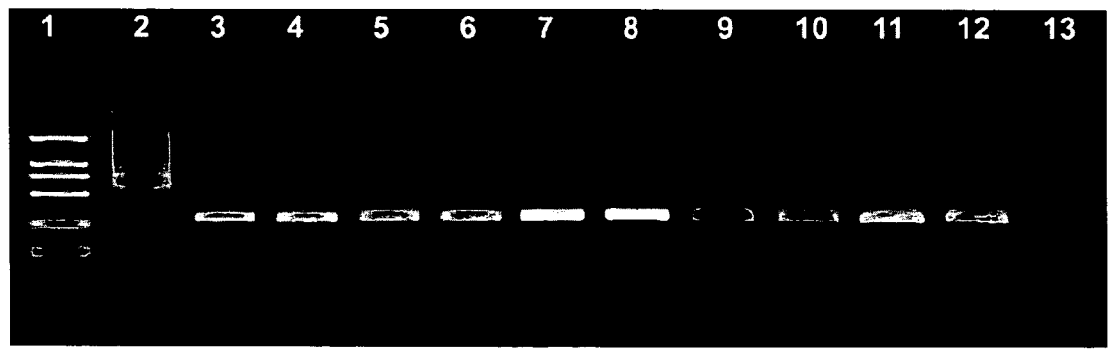
FIG. 11 illustrates the products of two-round PCR by using element titanium, element nickel, element bismuth, element stibium, element selenium and element chromium as optimized materials run on an agarose gel according to the preferred embodiment of the present invention.

As shown in FIG. 11, the optimized materials contained in reactions are as below: a piece of nickel filament (lane 3 and 4), one bismuth spherical particle (lane 5 and 6), one stibium spherical particle (lane 7 and 8), selenium powder (lane 9 and 10), and chrome powder (lane 11 and 12). The reaction of lane 2 does not contain optimized material, the reaction of lane 13 does not contain DNA template, and lane 1 is DNA marker (2000 bp, 1000 bp, 750 bp, 500 bp, 250 bp, and 100 bp). The amplification result of PCR containing element titanium, element nickel, element bismuth, element stibium, element selenium and element chromium shows clear bands corresponding to the targets. However, the amplification results of PCR without optimized material show non-specific PCR products as a broad molecular size distribution. Notably, an increase in specificity by using element titanium, element nickel, element bismuth, element stibium, element selenium and element chromium is seen in this experiment.

Example 12

Optimizing two-round PCR by using chromium powder as optimized material

In this example, the same two-round PCR system as Example 6 is used.

Every round of amplification program is performed as the same as Example 1, and thereafter the products of PCR reactions are analyzed by agarose gel electrophoresis.

The size of chromium powder used in this example is about 200 mesh.

Figure 12:
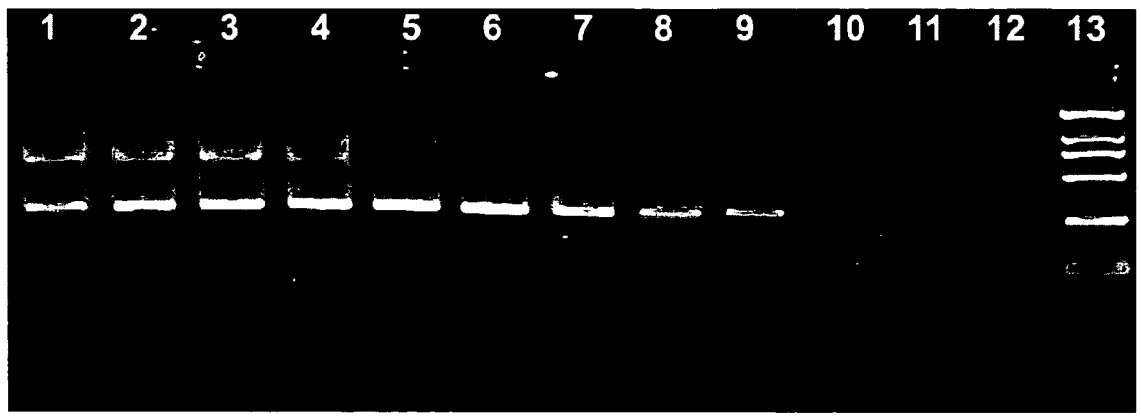
FIG. 12 illustrates the products of two-round PCR by using chromium powder as optimized material run on an agarose gel according to the preferred embodiment of the present invention.

As shown in FIG. 12, the amounts of about 200 mesh chromium powder contained in reactions are as below: 150 μg (lane 2), 300 μg (lane 3), 450 μg (lane 4), 600 μg (lane 5), 750 μg (lane 6), 900 μg (lane 7), 1000 μg (lane 8), 1200 μg (lane 9), 1500 μg (lane 10) and 2000 μg (lane 11), and the reaction of lane 1 does not contain optimized material, the reaction of lane 12 does not contain DNA template, and lane 13 is DNA marker (2000 bp, 1000 bp, 750 bp, 500 bp, 250 bp, and 100 bp). The amplification result of PCR containing suitable amount of chromium powder shows a single predominant band corresponding to the 283-bp target. However, the amplification results of PCR without chromium powder show non-specific PCR products as a broad molecular size distribution. The suitable amount of chromium powder is 450 μg to 1500 μg, and the preferred amount of chromium powder is 600 μg to 1200 μg.

Example 13

Achieving rapid PCR amplification by using colloid gold as optimized material

In this example, 300 ng of genome DNA of *Escherichia coli* is used as template, and two primers are used to amplify a 997-bp segment. The sequences of these two primers are: P1: 5'-CCAGCAGCCGCGGTAATACG-3'; P2: 5'-ATCG-GTTACCTTGTTACGACTTC-3'.

The rapid PCR is performed as follows: 30 cycles of 98° C. for 1 second (denaturing), 60° C. for 15 seconds (annealing); followed by a final extension at 72° C. for 5 minutes, and thereafter the products of PCR reactions are analyzed by agarose gel electrophoresis.

Colloid gold (10 nm, 0.01% $HAuCl_4$) is purchased from Sigma.

Figure 13:
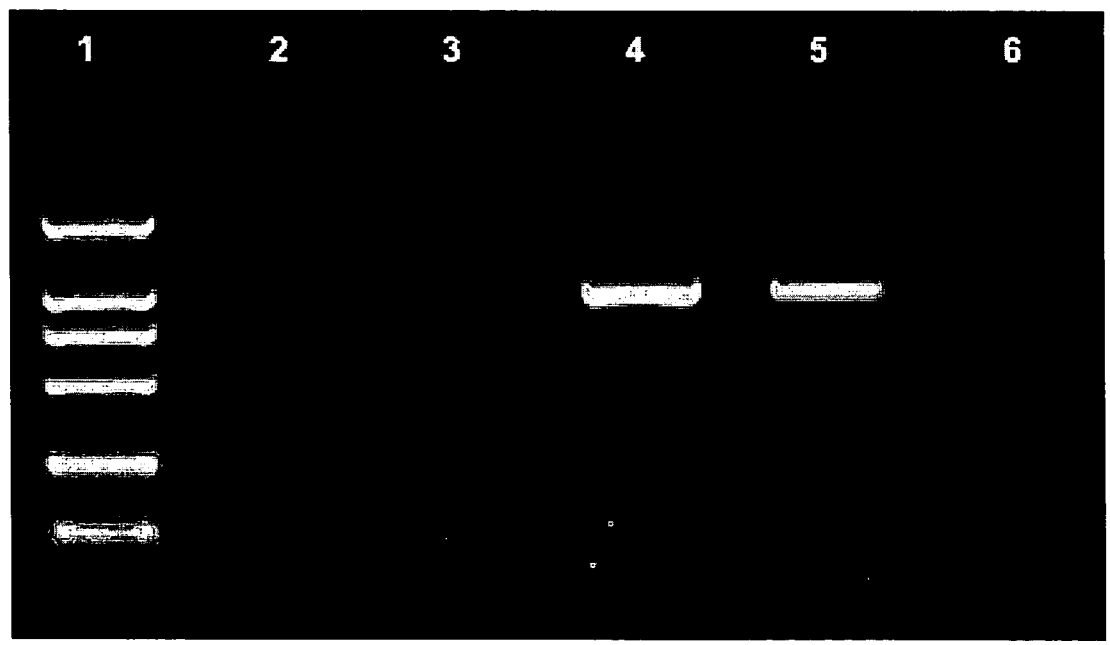
FIG. 13 illustrates the products of rapid PCR amplification by using colloid gold as optimized material run on an agarose gel according to the preferred embodiment of the present invention.

As shown in FIG. 13, reactions of lane 2, and 3 do not contain colloid gold; each reaction of lane 4 and 5 contains 0.5 μL colloid gold as optimized material; reaction of lane 6 does not contain template, and lane 1 is DNA marker (2000 bp, 1000 bp, 750 bp, 500 bp, 250 bp, and 100 bp). The amplification results of rapid PCR containing colloid gold (lane 4 and 5) show a single predominant band corresponding to the target. However, the amplification results of PCR without colloid gold (lane 2 and 3) do not show target band. In this example of rapid PCR, colloid gold enhances the specificity and efficiency, shortens the reaction time and increases the yields of target products. Rapid PCR is achieved with the help of colloid gold.

Example 14

Optimizing two-round PCR by using the mixture of titanium powder and colloid gold or the mixture of titanium powder and chromium powder as optimized materials In this example, the same two-round PCR system as Example 6 is used.

Every round of amplification program is performed as the same as Example 1, and thereafter the products of PCR reactions are analyzed by agarose gel electrophoresis.

The optimized materials used in this example are: colloid gold (10 nm, 0.01% $HAuCl_4$), chromium powder (200 mesh), titanium powder (200-300 mesh)

Figure 14:
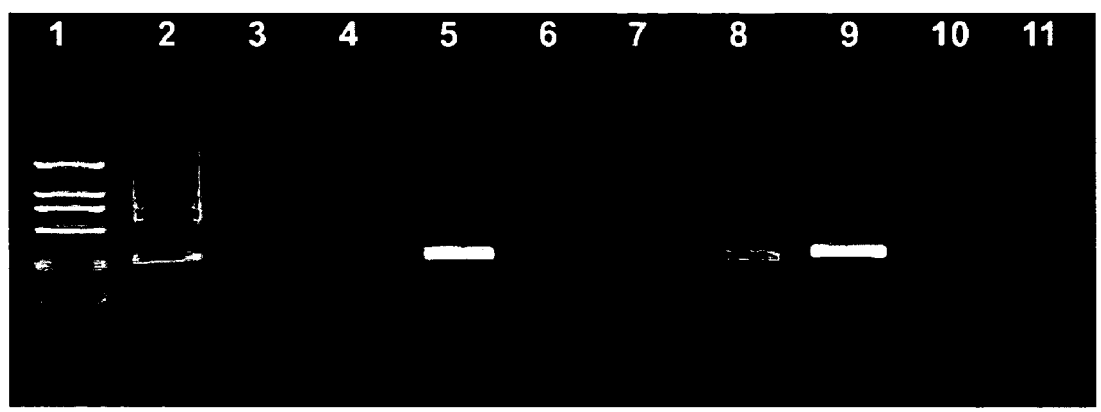
FIG. 14 illustrates the products of two-round PCR by using the mixture of titanium powder and colloid gold or the mixture of titanium powder and chromium powder as optimized materials run on an agarose gel according to the preferred embodiment of the present invention.

As shown in FIG. 14, the amounts of optimized materials contained in reactions are as below: 20 μg titanium powder and 1200 μg chromium powder (lane 3), 800 μg titanium powder and 300 μg chromium powder (lane 4), 20 μg titanium powder and 300 μg chromium powder (lane 5), 800 μg titanium powder and 1200 μg chromium powder (lane 6), 0.3 μL colloid gold and 800 μg titanium powder (lane 7), 1.6 μL colloid gold and 20 μg titanium powder (lane 8), 0.3 μL colloid gold and 20 μg titanium powder (lane 9), and 1.6 μL colloid gold and 800 μg titanium powder (lane 10). The reaction of lane 2 does not contain optimized material, the reaction of lane 11 does not contain DNA template, and lane 1 is DNA marker (2000 bp, 1000 bp, 750 bp, 500 bp, 250 bp, and 100 bp).

The amplification result of PCR containing suitable amount of the mixture of optimized materials mentioned above shows a single predominant band corresponding to the 283-bp target. However, the amplification results of PCR without chromium powder show non-specific PCR products as a broad molecular size distribution.

REFERENCES

U.S. Patent Documents

| | | | |
|---|---|---|---|
| 5545539 | August, 1996 | Miller et al. | 435/91.2 |
| 5646019 | July, 1997 | Nielson et al. | 435/91.5 |
| 5773257 | June, 1998 | Nielson et al. | 435/91.1 |
| 5846716 | December, 1998 | Miller et al. | 435/6. |
| 6783940 | August, 2004 | McLaughlin et al. | 435/6. |

OTHER REFERENCES

Henke, W.; Herdel, K. et al. (1997), "Betaine improves the PCR amplification of GC-rich DNA sequences", Nucleic Acids Res Vol. 25(19) No. 3957-8.

Sarkar, G.; Kapelner, S. et al. (1990), "Formamide can dramatically improve the specificity of PCR", Nucleic Acids Res Vol. 18(24) No 7465.

Bachmann, B.; Luke, W. et al. (1990), "Improvement of PCR amplified DNA sequencing with the aid of detergents", Nucleic Acids Res Vol. 18(5) No. 1309.

Winship, P. R. (1989), "An improved method for directly sequencing PCR amplified material using dimethyl sulphoxide", Nucleic Acids Res Vol. 17(3) No. 1266.

Nagai, M.; Yoshida, A. et al. (1998), "Additive effects of bovine serum albumin, dithiothreitol, and glycerol on PCR", Biochem Mol Biol Int Vol. 44(1) No. 157-63.

Kovarova, M.; Draber, P. (2000), "New specificity and yield enhancer of polymerase chain reactions", Nucleic Acids Res Vol. 28(13) No. E70.

Chase, J. W.; Williams, K. R. (1986), "Single-stranded DNA binding proteins required for DNA replication", Annu Rev Biochem Vol. 55, No. 103-36.

Chou, Q. (1992), "Minimizing deletion mutagenesis artifact during Taq DNA polymerase PCR by *E. coli* SSB", Nucleic Acids Res Vol. 20(16) No. 4371.

Varadaraj, K.; Skinner, D. M. (1994), "Denaturants or cosolvents improve the specificity of PCR amplification of a G+C-rich DNA using genetically engineered DNA polymerases", Gene Vol. 140(1) No. 1-5.

Haikuo Li, J. H., Junhong Lv et al. (2005), "Nanoparticle PCR: Nanogold-Assisted PCR with Enhanced Specificity", Angewandte Chemie Vol. 44, No. 2256-2262.

What is claimed is:

1. A method for optimizing PCR amplification, comprising the steps of:
   (a) preparing or obtaining gold as an elementary substance material;
   (b) sterilizing said elementary substance material;
   (c) adding said elementary substance material into a PCR system for amplification, wherein said elementary substance material is added before or during PCR amplification;
   (d) testing an amplification result by agarose gel electrophoresis; and
   (e) separating said elementary substance material from said PCR system so as to obtain PCR products.

2. The method for optimizing PCR amplification, as recited in claim 1, wherein said elementary substance material is prepared with predetermined forms selected from a group consisting of filament form, sheet form, particle form, powder form, colloid form and any other irregular form.

3. The method for optimizing PCR amplification, as recited in claim 1, wherein said PCR system is 25 uL.

4. The method for optimizing PCR amplification, as recited in claim 3, wherein the step (c) further comprises a step (c-1) for immersing fully said filament form, said sheet form and said particle form of said elementary substance material within a PCR solution.

5. The method for optimizing PCR amplification, as recited in claim 4, wherein said PCR solution is contained within a PCR tube, a height of said solution surface is lower than 0.6 cm from a bottom of said PCR tube.

6. The method for optimizing PCR amplification, as recited in claim 3 wherein said step (e) further comprises a step for directly aspirating said PCR system to remove said filament form, said sheet, and said irregular form of said elementary substance materials.

7. The method for optimizing PCR amplification, as recited in claim 3, wherein said step (e) further comprises a step for centrifuging said PCR system at a low speed and then harvesting a supernatant to remove said powder form and said particle form of said elementary substance materials.

8. The method for optimizing PCR amplification, as recited in claim 3, wherein said step (e) further comprises a step for overnight freezing at a temperature of −20° C. and centrifuging said PCR solution at a high speed to remove said colloids form of said elementary substance material.

9. The method for optimizing PCR amplification, as recited in claim 3, wherein said step (c) further comprises a step for adding 50 µg-5000 µg said powder form of said elementary substance material into said PCR system.

10. The method for optimizing PCR amplification, as recited in claim 3, wherein said step (c) further comprises a step for adding 0.06 µL-6 µL said colloid form of said elementary substance material into said PCR system.

11. The method for optimizing PCR amplification, as recited in claim 3, wherein said step (c) further comprises a step for adding 2 mg-5 mg gold powder into said PCR system.

12. The method for optimizing PCR amplification, as recited in claim 3, wherein said step (c) further comprises a step for adding 0.06 µL-0.5 µL colloid gold (5 nm, 0.01% HAuCl4) into said PCR system.

13. The method for optimizing PCR amplification, as recited in claim 3, wherein said step (c) further comprises a step for adding 0.08 µL-0.16 µL colloid gold (5 nm, 0.01% HAuCl4) into said PCR system.

14. The method for optimizing PCR amplification, as recited in claim 3, wherein said step (c) further comprises a step for adding 0.5 µL-2.5 µL colloid gold (10 nm, 0.01% HAuCl4) into said PCR system.

15. The method for optimizing PCR amplification, as recited in claim 3, wherein said step (c) further comprises a step for adding 0.8 µL-6.0 µL colloid gold (20 nm, 0.01% HAuCl4) into said PCR system.

16. The method for optimizing PCR amplification, as recited in claim 15, wherein said step (c) further comprises a step for adding 0.5 µL-1.6 µL colloid gold (10 nm, 0.01% HAuCl4) into said PCR system.

17. The method for optimizing PCR amplification, as recited in claim 3, wherein said step (C) further comprises a step for adding 0.8 µL-3.5 µL colloid gold (20 nm, 0.01% HAuCl4) into said PCR system.

18. The method for optimizing PCR amplification, as recited in claim 3, wherein said step (c) further comprises a step for adding said element gold with surface area at least 4 $mm^2$ in filament form, sheet form and particle form into said PCR system.

* * * * *